United States Patent [19]
Wingrove

[11] Patent Number: 6,064,911
[45] Date of Patent: May 16, 2000

[54] DEVICE USING BOTH HVPC AND NMS ELECTROTHERAPY

[75] Inventor: Robert C. Wingrove, Shoreview, Minn.

[73] Assignee: Rehabilicare, Inc., New Brighton, Minn.

[21] Appl. No.: 08/907,743

[22] Filed: Aug. 8, 1997

[51] Int. Cl.[7] .............................. A61N 1/34; A61N 1/36; A61N 1/18
[52] U.S. Cl. ................................ 607/46; 607/66; 607/48
[58] Field of Search .................................. 607/46, 48, 49, 607/66

[56] References Cited

U.S. PATENT DOCUMENTS

| | | |
|---|---|---|
| 4,324,253 | 4/1982 | Greene et al. ............................ 607/46 |
| 4,392,496 | 7/1983 | Stanton . |
| 4,690,146 | 9/1987 | Alon ......................................... 607/66 |
| 5,269,304 | 12/1993 | Matthews ................................. 607/46 |
| 5,514,165 | 5/1996 | Malaugh et al. .......................... 607/46 |
| 5,776,171 | 7/1998 | Peckham et al. . |
| 5,800,458 | 9/1998 | Wingrove . |

*Primary Examiner*—William E. Kamm
*Assistant Examiner*—Carl H. Layno
*Attorney, Agent, or Firm*—Patterson & Keough, P.A.

[57] ABSTRACT

An electrotherapy device which provides neuromuscular and high voltage pulsed galvanic physiological stimulation and includes a common cabling assembly and a common electrode assembly for simultaneously accommodating the neuromuscular and high voltage pulsed galvanic stimulation modes, whereby neuromuscular and pulsed galvanic stimulation may be provided to a patient simultaneously.

63 Claims, 13 Drawing Sheets

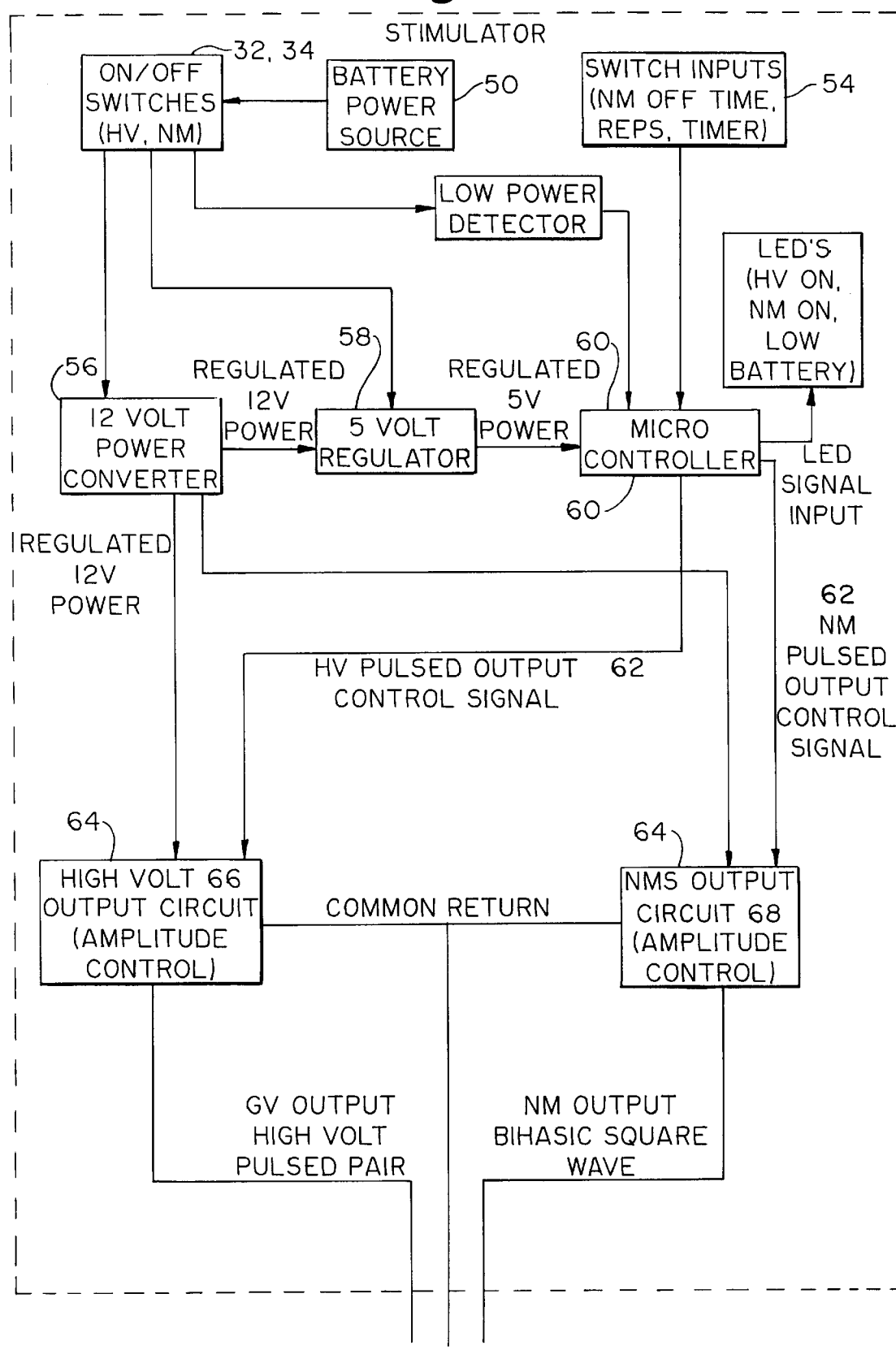

Fig. 10

NM TURNED ON 10 MIN. AFTER HV
TURNED ON AND RUNS 28 MIN.
HV ON FOR 2 MIN. AFTER NM SHUTS OFF AT 100
HZ AND RAMPS TO 4 HZ IN 12 SEC., RUNS FOR 14
100HZ | 4HZ | MIN. 48 SEC'S. AND SHUTS OFF.

0  15  30  45  60  75  90
MINUTES
AUTO MODE

Fig. 11

NM TURNED ON 10 MIN. AFTER HV
TURNED ON AND RUNS 28 MIN.
HV SET FOR 90 MIN. AFTER 75 MIN. AT 100
100 HZ | 4 HZ | HZ AND RAMPS TO 4 HZ IN 12 SEC., RUNS
FOR 14 MIN/48 SEC'S. AND SHUT OFF.

0 15 30 45 60 75 90
MINUTES
INCREMENTAL MODE

Fig. 12

13 MIN | 28 MIN
NM SET UP FOR 28 MIN. WILL ONLY RUN FOR 13 MIN.
HV ON FOR 30 MIN. AT 100 HZ AND RAMPS TO 4 HZ
17 MIN | 4 | IN 12 SECS., RUNS FOR 14 MIN. 48 SEC'S. AND
100 HZ | 4 HZ | SHUTS OFF.

0 15 30 45 60 75 90
MINUTES
INCREMENTAL MODE

Fig. 13

NM SET UP FOR 28 MIN. WILL ONLY RUN FOR 13 MIN.
TIMER IS SET FOR 30 MIN. AND THE HV MODE OFF.

0  15  30  45  60  75  90
MINUTES
INCREMENTAL MODE

DEVICE USING BOTH HVPC AND NMS ELECTROTHERAPY

TECHNICAL FIELD

The present invention relates to electrical devices for physiological application of electricity for therapeutic purposes, e.g., to relieve pain and/or activate muscle fibers.

BACKGROUND

As reflected in U.S. Pat. No. 4,144,893 (Hickey), U.S. Pat. No. 4,177,819 (Kofsky et al.), U.S. Pat. No. 4,887,603 (Morawetz et al.), U.S. Pat. No. 4,926,865 (Oman), U.S. Pat. No. 4,977,895 (Tannenbaum) and U.S. Pat. No. 5,010,896 (Westbrook), the therapeutic use of electricity is known. The devices disclosed in these patents typically include a power source, a control mechanism, and a pair of electrodes for connection to a subject. They all produce electrical pulses having selected characteristics for therapeutic purposes, e.g., to reduce pain (Morawetz et al.) or for treating edema, muscle spasms, and sprains (Westbrook).

Refinements of neuromuscular stimulating devices are disclosed in U.S. Pat. No. Re. 32,091 (Stanton) and U.S. Pat. No. 4,690,146 (Alon). The Stanton device is a dual channel stimulator whereby simultaneous neuromuscular stimulation may be provided at two sites, and the Alon stimulator includes a plurality of interconnected electrical stimulation units each with at least a pair of electrodes whereby synchronous or asynchronous stimulation of a desired muscle or muscle group may be achieved.

U.S. Pat. No. 5,514,165 (Malaugh et al.) discloses a further refinement in the art of electrotherapy. The Malaugh et al. stimulation unit includes a high voltage pulsed current ("HVPC") electrotherapy stimulation device for providing short duration low ampere high voltage constant charge HVPC pulses to a patient to reduce pain and a neuromuscular stimulation ("NMS") electrotherapy device for providing constant current NMS pulses to a patient to re-educate and prevent atrophy of muscle tissue. A stated advantage of the Malaugh et al. unit is that it provides both HVPC and NMS electrotherapy from a single device.

While the preceding patents reveal advances in the art of electrotherapy and its use, none discloses or provides a neuromuscular stimulation device for the simultaneous reduction of pain and strengthening and re-educating of muscle, i.e., none discloses a device wherein neuromuscular and high voltage pulsed outputs are provided at the same time, and none discloses a device having an electrode configuration enabling the simultaneous providing of such electrotherapy.

SUMMARY

One embodiment of the present invention relates to an electrotherapy device comprising a first electrical stimulation device and a second electrical stimulation device. The electrotherapy device further comprises a microcontroller to provide electrical stimulation to a patient from both the first and second electrical stimulation devices simultaneously.

Another embodiment of the present invention provides a device for simultaneously delivering neuromuscular and high-voltage pulsed galvanic stimulation to a patient, and encompasses a non-invasive method of electrotherapy using the device for simultaneous rehabilitation and pain relief.

The electrotherapy device of the present invention comprises a stimulator which simultaneously outputs neuromuscular stimulation (also referred to herein as "NMS") and high-voltage pulsed galvanic stimulation (also referred to herein as "HVPG").

More specifically, the electrotherapy device of the present invention comprises a non-invasive electrical stimulator which combines neuromuscular stimulation having a biphasic square wave output with high volt pulsed galvanic stimulation having a monophasic pulsed pair output and is operable in both stimulation modes simultaneously. The device of the present invention comprises a power source, power converter, voltage regulator, a micro-controller, including control means, a high voltage output circuit, a neuromuscular voltage output circuit, and an electrode arrangement for receiving the high voltage and neuromuscular output voltages. The device is adapted to be used as a fixed-parameter muscle stimulator, a fixed-rate, high-volt galvanic stimulator, or the stimulator outputs can be combined to provide simultaneous mixed stimulation. In each instance, the same electrode arrangement may be used.

An advantage of the present invention is that it provides the benefit of simultaneously administering HVPG stimulation for reducing pain and swelling and NMS stimulation (which may cause pain) used for increasing range of motion, exercising muscles, etc. The invention is particularly well-suited for post-operative and rehabilitative treatment of patients who have undergone knee replacement, surgical reconstruction or repair procedures (including ACL, arthroscopy, meniscectomy, patellar debridement, lateral release or the like). It may be used to treat knee injuries, patellar/femoral syndrome, arthritis sprains/strains, or any injury or disorder resulting in muscle atrophy of the upper leg and decreased range of motion of the knee. It is designed for use by orthopedic surgeons, general practice physicians, physical therapists, and patients themselves. Another advantage is that the invention provides for the use of a common electrode, thereby simplifying use of the unit for a caregiver or patient, and improving treatment compliance. The invention, particularly the simultaneous delivery of NMS and HVPG stimulation, shortens recovery and rehabilitation time. Generally, it is intended for use during the six to eight week post-operative period following reconstructive or other surgery to improve or maintain muscle tone, promote a full range of motion, and to reduce edema and pain. Generally, the device of the present invention will be used during three sessions per day, wherein the NMS mode will be on for approximately 15 minutes per session or for the desired number of repetitions (muscle contractions) and the HVPG mode will be on for about an hour per session.

Other features and advantages of the present invention will become more fully apparent and understood with reference to the following description and to the appended drawings and claims.

BRIEF DESCRIPTION OF THE DRAWINGS

FIG. 10 represents one operational setting of the present invention.

FIG. 11 represents another operational setting of the present invention.

FIG. 12 represents another operational setting of the present invention.

FIG. 13 represents another operational setting of the present invention.

DETAILED DESCRIPTION

With regard to means for fastening, mounting, attaching, or connecting the components of the present invention to form the electrotherapy device as a whole, unless specifically described as otherwise, such means are intended to encompass conventional fasteners such as machine screws, rivets, nuts and bolts, pins, and the like. Other fastening or attachment means appropriate for connecting components include adhesives or welding (e.g., for the housing) and soldering, the latter particularly with regard to circuitry and electrical connections. Unless specifically otherwise disclosed or taught, materials for making the components of the present invention may be selected from appropriate materials such as metal, metallic alloys, various plastics and the like.

In the following description, any references to right and left, top and bottom, upper and lower and horizontal and vertical are to be read and understood with their conventional meanings and with reference to viewing the embodiment of the electrotherapy unit of the present invention as shown in FIGS. 1a–d and 7. Elements or components common to depicted embodiments of the present invention are commonly numbered.

The electrotherapy device comprises a first electrical stimulation device (such as a high volt pulsed direct current stimulator), a second electrical stimulation device (such as a neuromuscular stimulator), and a controller to provide electrical stimulation to a patient from both the first and second electrical stimulation devices simultaneously. The electrotherapy device 10 further comprises a housing 20, electrical circuitry 21, and cable assembly 22.

Housing

Figure 1A:
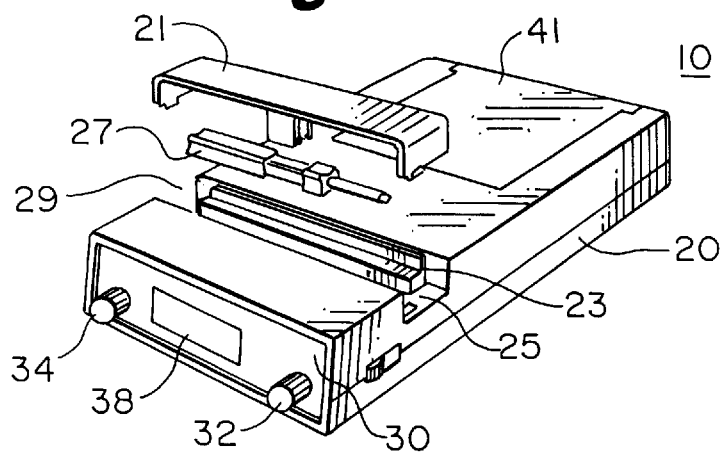
FIGS. 1a–d show the housing of the stimulator of the present invention.
Figure 1B:
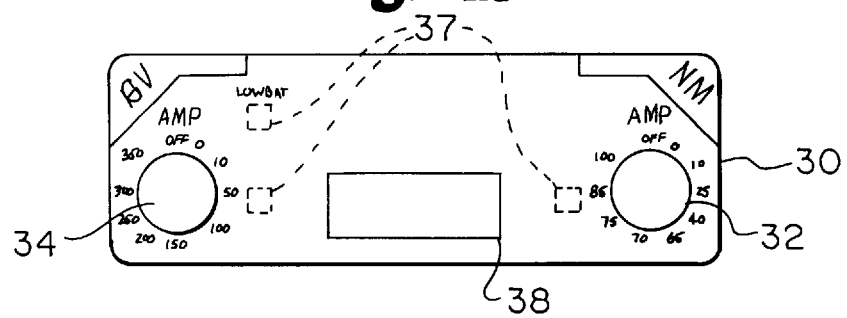

Referring then to the drawings, particularly FIGS. 1a–d, the electrotherapy stimulation device 10 comprises a box-like housing or case 20. Referring to FIGS. 1a and 1b, the housing 20 has a front panel 30 and includes at least two rotatable ON/OFF rotary switches with output amplitude adjustment 32, 34 for actuating and controlling (e.g., adjusting the amplitude of) NMS stimulation and HVPG stimulation. The front panel 30 of the housing 20 may include other switches such as a polarity switch, and it may be provided with appropriate display devices such as repetition counters, timers, power on and operative mode indicators 37 and the like. Plug or pin-receiving outlet 38 is available to receive the connector comprising part of the cable assembly 80 (which will be described later).

Figure 1C:
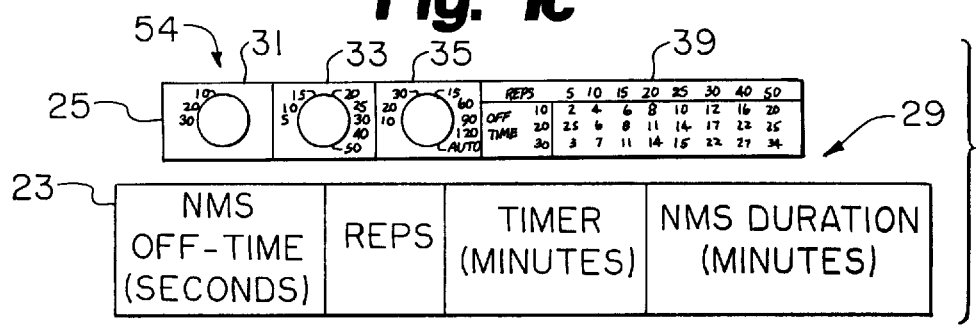

Continuing to refer to FIG. 1a, the housing 20 further comprises a removable cover portion 21 to access controls to modify NMS off-time, NMS repetitions, and a timer for setting the total number of minutes for the entire treatment. FIG. 1c shows the controls 25: the NMS off-time control 31, the repetition control 33, and the timer control 35. There is also an NMS duration table 39 that shows the selected number of repetitions and off-times between each of the repetitions.

Figure 1D:
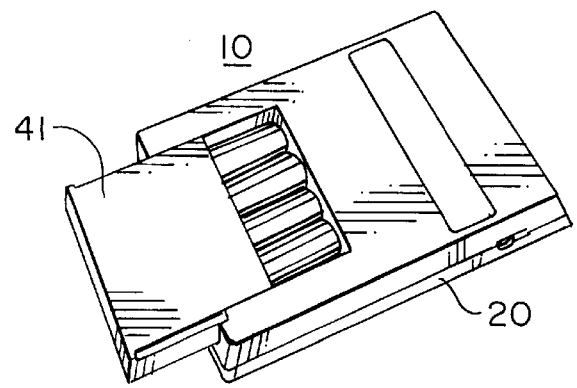

As shown in FIGS. 1a and 1d, a battery or power compartment 41 may be provided and accessed similarly. Batteries 50 may be placed in the battery compartment 41 to power the device 10.

Electrical Components and Circuits

Figure 2:
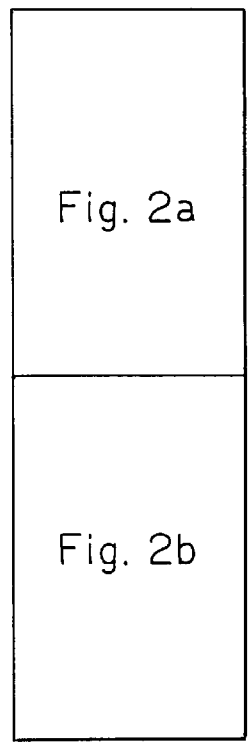
FIG. 2 is a block diagram depicting and representing components of the present invention.
Figure 2B:
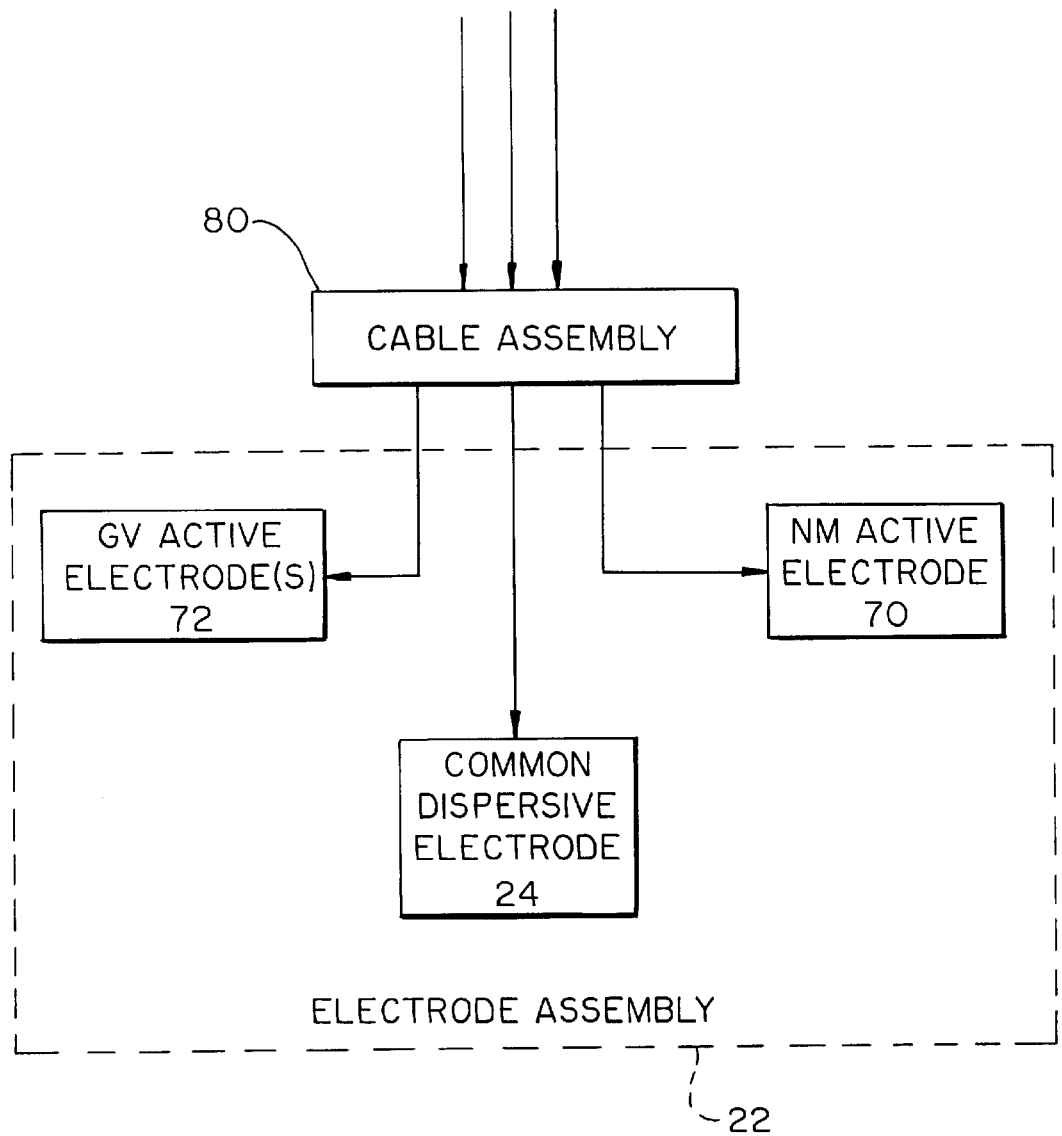

Referring to FIG. 2, the electrical components and circuitry of the present invention, housed substantially in the housing 20, are represented in diagram form. The stimulator device 10 of the present invention includes a power source 50 controlled by on-off switches 32, 34. Typically, four AA commercially available battery cells (see FIG. 1d), nickel cadmium or alkaline, are preferred, but the device could be adapted to run off an external power converter and a battery charging system may be incorporated therein. Switch inputs 54 are provided for controlling the operation of the unit. An internal power convertor 56 is incorporated, as is a voltage regulator 58. The components, and operation of the electrotherapy device as a whole, are controlled by a microcontroller unit 60 (for example, a Motorola 8-bit micro controller MC68HC705J1A or the like) which produces and transmits timing, repetition counting and trigger signals, represented at 62, thereby regulating and controlling the output circuits 64 of the present invention. The software will control the system timing requirements using the output of a 3.2768 MHz crystal oscillator or like clock. The output circuits 64 include a high voltage output circuit 66 for producing the high voltage pulsed galvanic output (referred to herein as HVPG) of the present invention and a neuromuscular output circuit 68 for producing the neuromuscular stimulation output (referred to herein as NMS) of the present invention. The electrode assembly 22 includes the common electrode 24, an NMS output electrode 70 and at least one, preferably one to four, HVPG electrodes 72.

NMS and HVPG Electrical Output

Figure 3A:
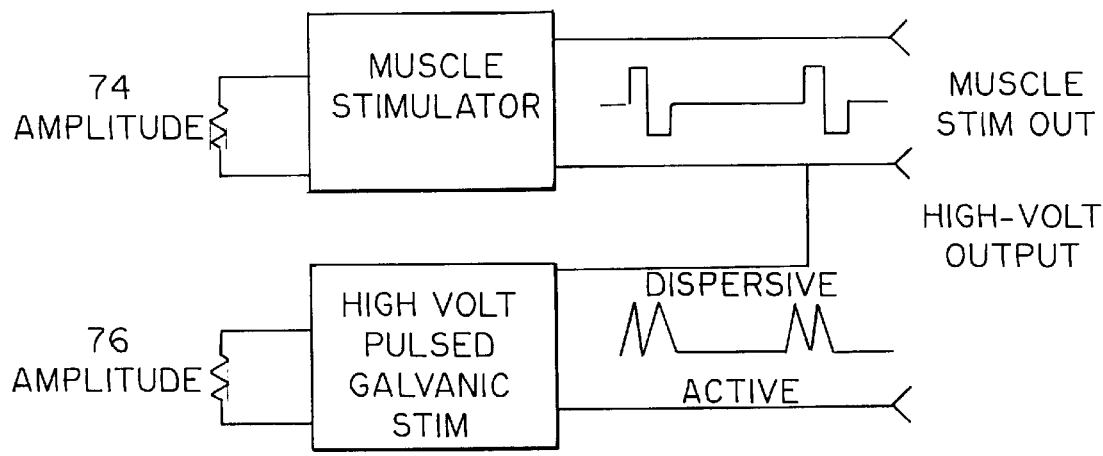
FIG. 3a and 3b are diagrammatic representations of the outputs of the NMS-HVPG stimulator device of the present invention.

The electrical output of the present invention is depicted in diagram form in FIG. 3a. The NMS output, indicated generally at 74, may be an asymmetric biphasic pulse output or a symmetrical biphasic square wave output, and the HVPG output, indicated generally at 76, may be a pulsed galvanic, monophasic exponential spike, delivered in pulse pairs 100 microseconds apart. More specifically, in the preferred embodiment of the present invention, the NMS modality output has the following characteristics:

Wave form: asymmetric biphasic pulse output or symmetrical biphasic square wave output.

Amplitude: 0 to 100 mA peak.

Pulse width: ramping from 0 to 300 microseconds.

Pulse rate: 33 Hz.

Ramp up time: 3 seconds.

On time: 10 seconds.

Ramp down time: 1 second.

Off time between stimulation cycles: adjustable, 10, 20, or 30 seconds.

Number of stimulation cycles: adjustable in increments of 5 repetitions from 5 repetitions to 30 repetitions and 40 and 50 repetitions (5,10,15,20,25,30,35,40, and 50 repetitions).

Further characteristics or features of the NMS modality include:

Single channel output.

Fixed cycle on-time with a fixed ramp up and ramp down time (3 seconds up, 10 seconds on, 1 second down are preferred, but may be varied).

Number of cycles (muscle contraction/stretch repetitions or time) selection.

Adjustable off-time between cycles selection.

On/Off rotary switch common with output amplitude adjustment.

On indicator (a LED is preferred) that pulse at the rate of stimulation (33 Hz) (rapid pulse) while delivering stimulation to the user; between repetition cycles it pulses at a rate of 100 pulses per second (slow pulse) to indicate that no NMS is being delivered to the user thereby causing the LED to be on for 0.5 seconds and off for 0.5 seconds during no stimulation.

The HVPG modality output has the following characteristics:

Wave form: pulsed galvanic, monophasic exponential spike, delivered in pulse pairs 100 microseconds apart.

Output voltage: 0 to 350 volts, adjustable.

Pulse width: 7 microseconds @ 50% peak.

Pulse pair frequency, 100 Hz.

Further characteristics or features of the HVPG modality include:

Single channel continuous output that will support one to four active electrodes.

Fixed rate output (100 pulse pair/second is preferred).

Timer to set the treatment period with an automatic shut off concluding the completion of this period.

On/Off rotary switch common with output amplitude adjustment 32, 34.

On indicator that is continuous.

Also, in the HVPG mode, a polarity switch may be used for the active electrode being negative with the dispersive electrode being positive.

Figure 3B:
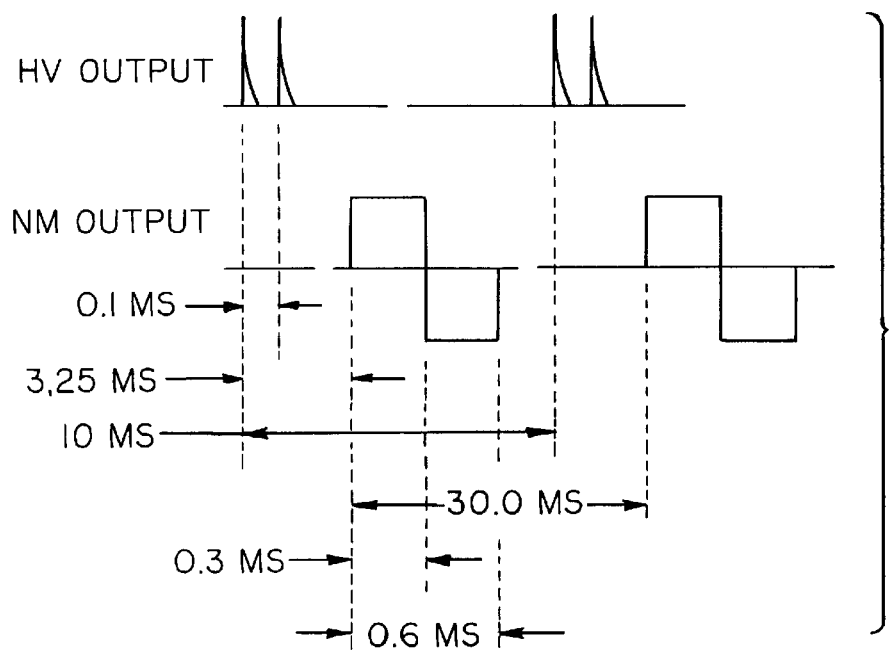

As shown in FIG. 3b, the timing and frequency of the High Volt Pulsed Galvanic idirect current) exponential spike and the Symmetric Biphasic Square Wave Neuromuscular wave is configured such that they do not overlap. This timing and frequency configuration allows HVPG and NMS stimulation to occur simultaneously and independently. The timing and the frequency can be configured such that HVPG spikes and NMS pulses (some or all) can occur at the same time (fall on top of each other). This still would allow NMS and HVPG stimulation to occur simultaneously and independently because the pulses are directed to discrete HVPG and NMS active electrodes of the electrode set (22) which are positioned on the anatomy to produce the desired effect. However this would cause a heavy drain on the power source when the pulses occur at the same time. Also the charge per pulse could exceed recommended treatment limits at higher output amplitudes.

Cable Assembly and Arrangement

Figure 4:
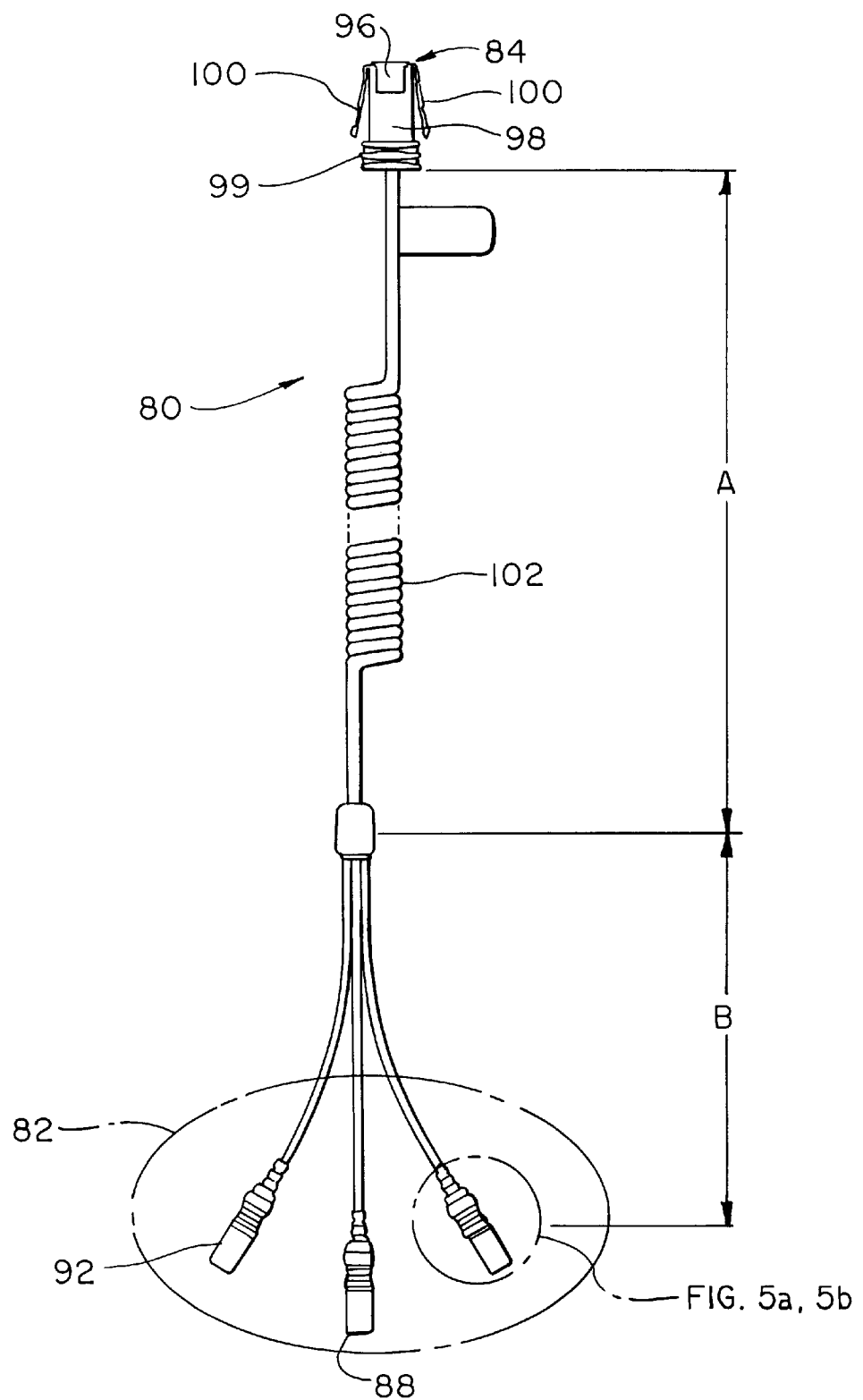
FIG. 4 depicts an embodiment of the cable assembly for use in the present invention.
Figure 5A:
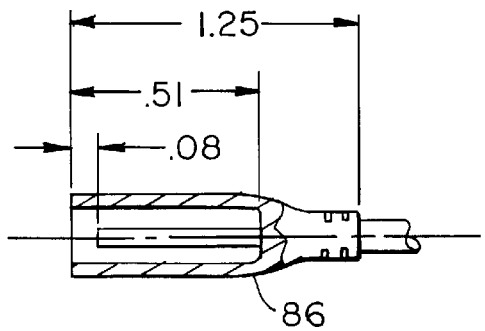
FIG. 5a and 5b depict a distal connector of the cable assembly.
Figure 5B:

With reference to FIG. 4, an embodiment of the cabling assembly 80 will be described. The cable assembly 80 connects the output of the stimulator 10 to the respective electrodes of the electrode assembly 22, and includes distal connectors 82 and a proximal connector 84. FIGS. 5a and 5b show a distal connector 86, 88, 92 which are substantially identical. Typically, one of the distal connectors may be dedicated to the active NMS electrode 90 (shown in FIG. 9a) one distal connector 88 may be dedicated to the common dispersive electrode (shown at 24 in FIG. 9a) and one distal connector 92 may be dedicated to the HVPG electrode or electrodes (shown at 94 in FIG. 9a).

Figure 6A:
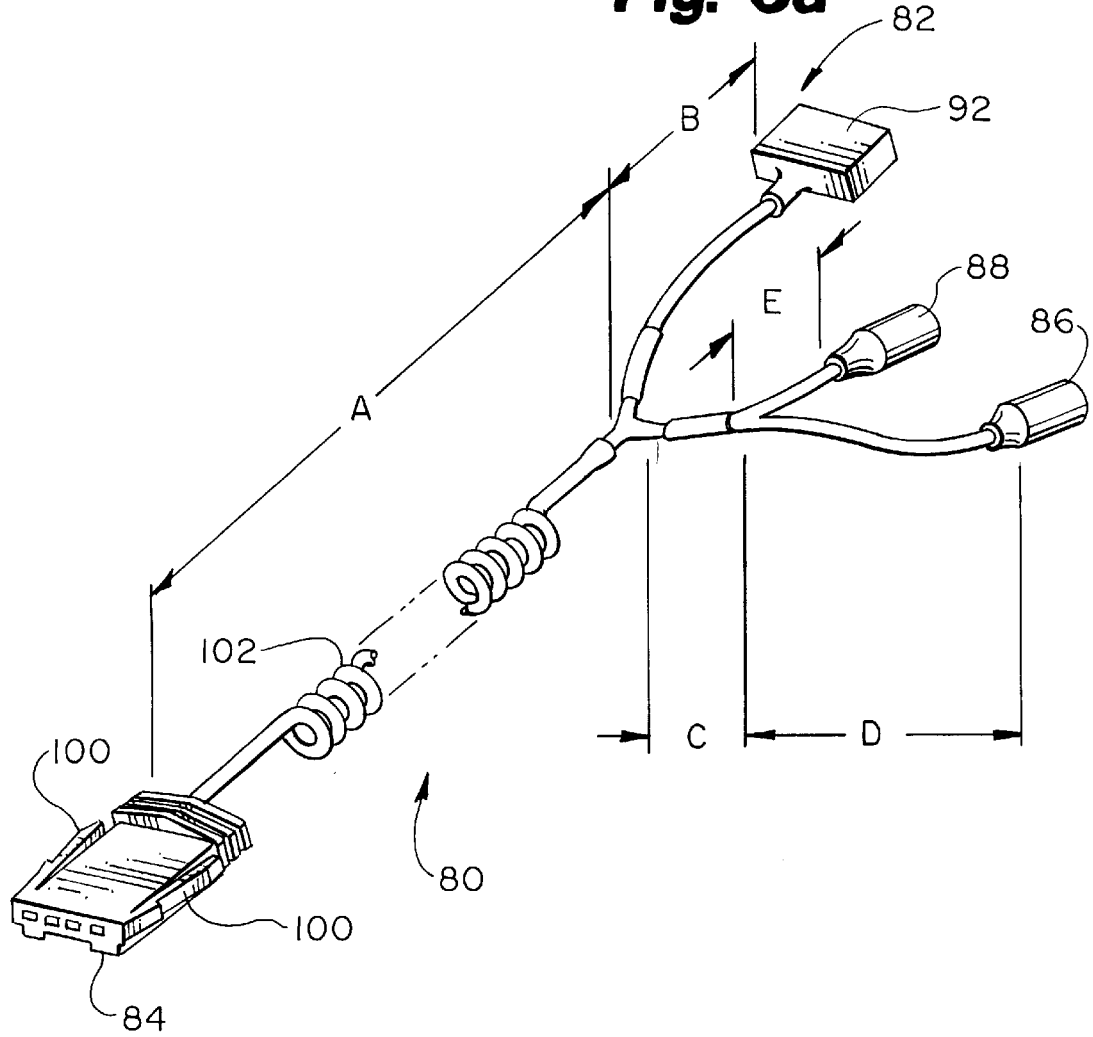
FIG. 6a–b depict the cable/connector assembly for use in the present invention.
Figure 6B:
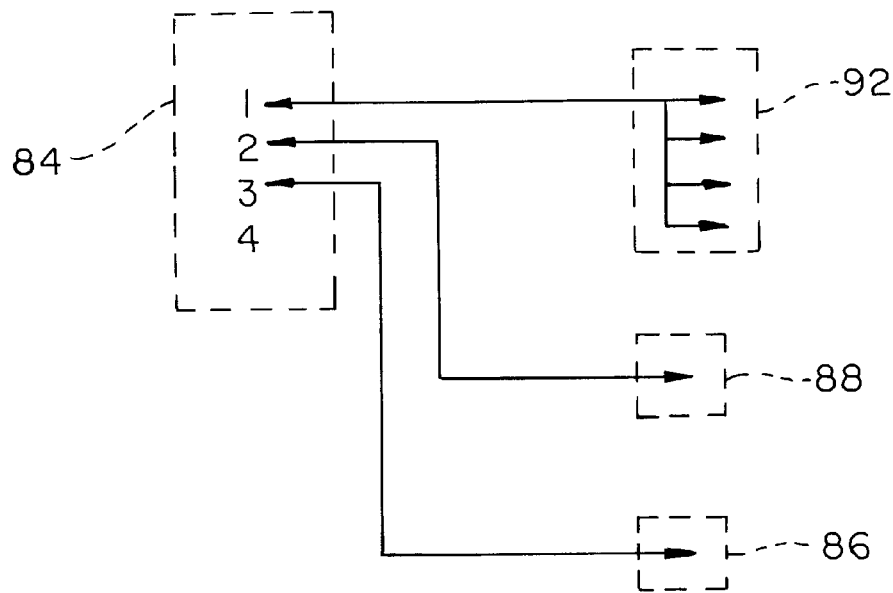
Figure 7:
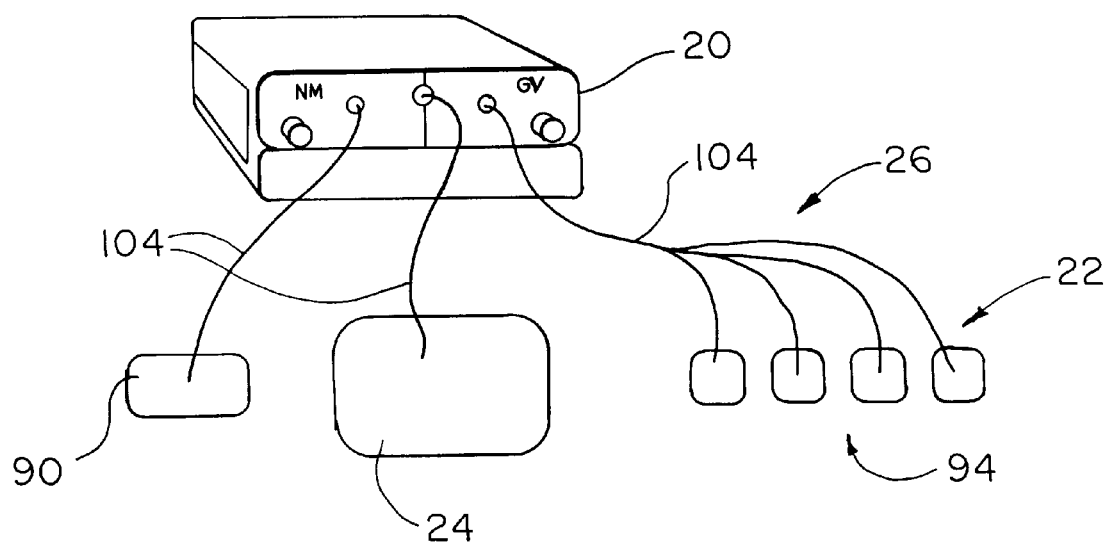
FIG. 7 depicts an alternate design for a stimulation unit of the present invention as it might be positioned for use, with the electrode assembly connected to the housing.

Alternatively, as shown in FIGS. 6a and 6b, connector 92 may be a multi-pin connector. This type of connector would be used when the HVPG electrodes are not connected to a common electrode connector.

The cable assembly 80 includes a proximal connector 84. In one embodiment of the proximal connector 84 shown in FIG. 4, the connector 84 has a body 98 with a pair of resilient, bi-lateral resilient locking members 100, a pin receiving end 96 and a plug end 99. The pin receiving end 96 is adapted to receive pins located in the plug receiving outlet 38 of stimulator 10. Also, a Molex C-Grid SL™ 70066 and 70400 latch connector may be used as a proximal connector 84. The Molex latch connector comprises a crimp housing and connector assembly. Also, a wire to board shrouded header (also by Molex, number 70555 or a Berg. Part No. 630099) may be used as part of the plug receiving outlet 38 for receiving the proximal connector 84.

Referring to FIGS. 5, 6a and 6b, the proximal connector 84 and the distal connectors 82 are connected by a cable 102. The cable 102 permits the output of the stimulator 10 to be communicated to the electrodes attached to the distal connectors 82. In one embodiment, a coiled multi-conductor cable 102 is used. In another embodiment (see FIG. 7), the electrodes may be connected to the stimulator 10 using three separate cables, each identified at 104.

Software

Figure 8:
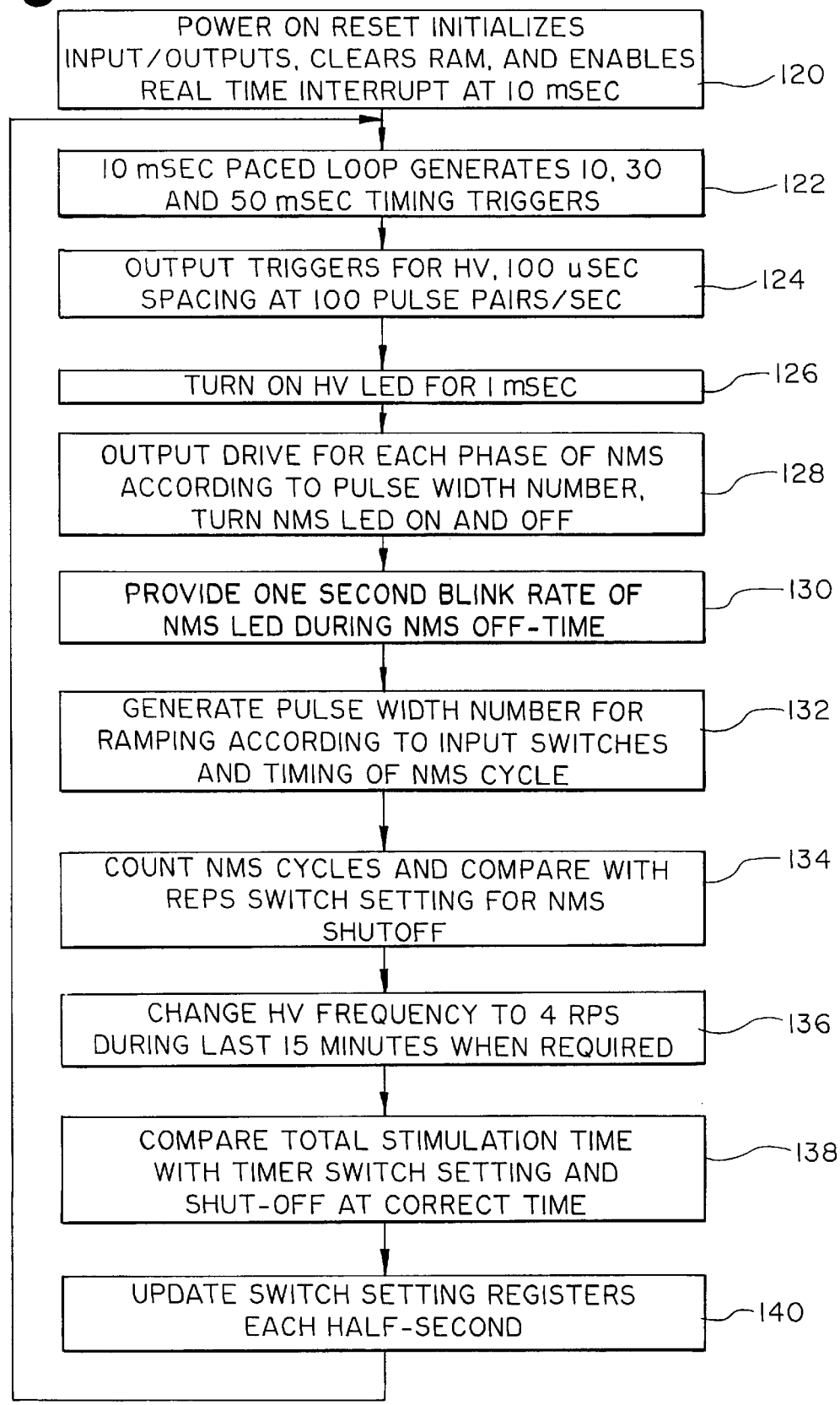
FIG. 8 is a simplified block diagram illustrating the basic software program flow of the operation of the electrotherapy stimulator device of the present invention.

FIG. 8 depicts the basic program flow of the operational software of the electrotherapy stimulator device of the present invention as the steps the microcontroller undertakes when the unit is operational. Referring to FIG. 8, the program flow of the software may be outlined as follows. At block 120, power on/reset initializes input and outputs, clears the RAM and enables real time interrupt at 10 ms. The programs flows to block 122 wherein a 10 ms pace loop generates 10, 30, and 50 ms timing triggers. At block 124, the program provides output triggers for HVPG, at 100 ms spacing, and at block 126, the HVGP LED is turned on for 1 ms. At block 128, the program actuates output drive for each phase of NMS, according to the pulse width number, and, at function block 130, turns the NMS LED on when NMS stimulation is being delivered and turns the NMS LED off when NMS stimulation is not being delivered. At 100 Hz, the LED will be on for ½ second and off for ½ second, thereby having a 1 second blink rate during NMS off time. As represented in block 132, the program generates pulse width numbers for ramping according to the input switches and the timing of the NMS cycle, and counts the NMS cycles and compares them with the switch setting for NMS shut off at, block 134. As represented at block 136, during the last 15 minutes, when required as determined by the timer setting, the program changes the HVPG frequency to 4 Hz. The program compares total stimulation time with the timer switch setting and initiates a shut off at a correct time as represented at block 138, and updates the switch setting registers each half second at block 140. As represented by the arrow 142, this flow continues as long as the power is on until the microprocessor shuts down as determined in block 138.

Figure 9A:
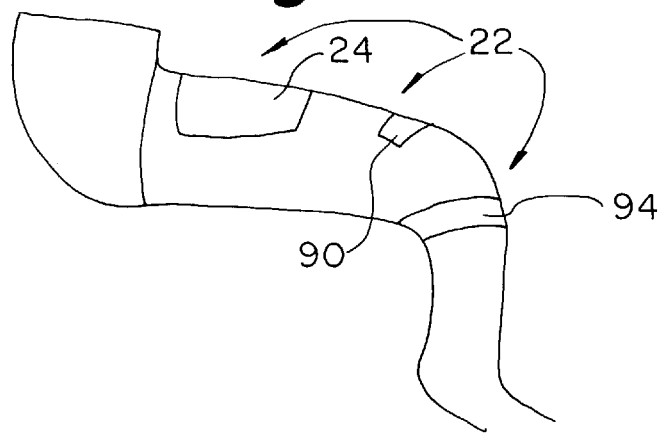
FIG. 9a depicts one possible arrangement of the electrode assembly of the present invention on a patient's leg.

FIG. 9a depicts one typical or representative disposition of the electrodes 22 of the present invention when it is in use to provide NMS and HVPG stimulation simultaneously. The electrodes are depicted on a person's leg. The high voltage HVPG active electrode (or electrodes) 94 are depicted below the person's knee, while the active muscle stimulation electrode 90 is positioned above the person's knee. The common or dispersive electrode 24 is shown above the muscle stimulation active electrode adjacent a person's thigh.

Figure 9B:
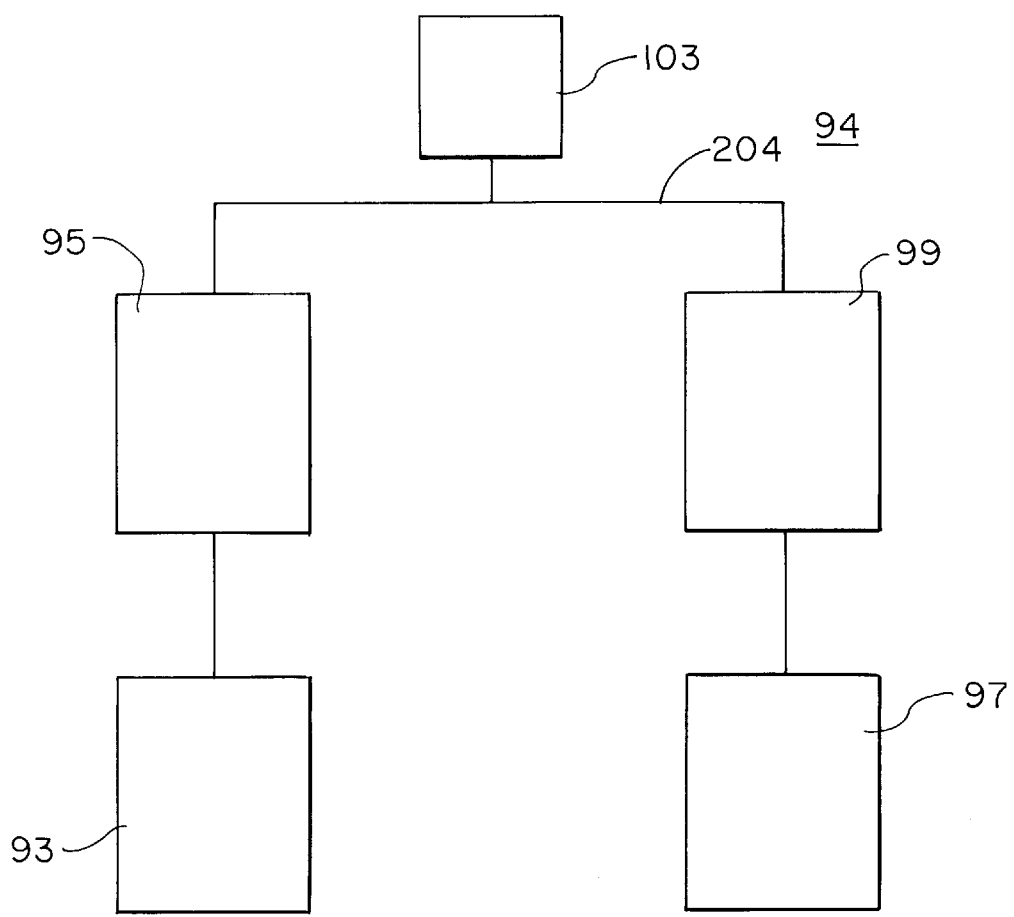
FIGS. 9b–f depict various embodiments of the HVPG electrode assembly.

FIGS. 9b–f show alternate arrangements for the active HVPG electrode assembly 94 that would connect to distal connector 92. FIG. 9b shows two pairs of electrodes, 93, 95, 97, 99, with each pair of electrodes connected in series via lead wire 204. The two pairs are connected to a HVPG electrode assembly connector 103 via lead wires 204. The connector 103 is adapted to be connected to connector 92, thereby enabling the output from the stimulator 10 to be output to the patient via the electrodes 93, 95, 97, 99. In the embodiment shown in FIG. 9b, electrodes 93, 95 would be attached to the right side of the leg, just below the knee, with one electrode placed in the front and one electrode placed in the back. Similarly, electrodes 97, 99 would be attached to the left side of the leg, just below the knee, with one electrode placed in the front and one electrode placed in the back.

Figure 9C:
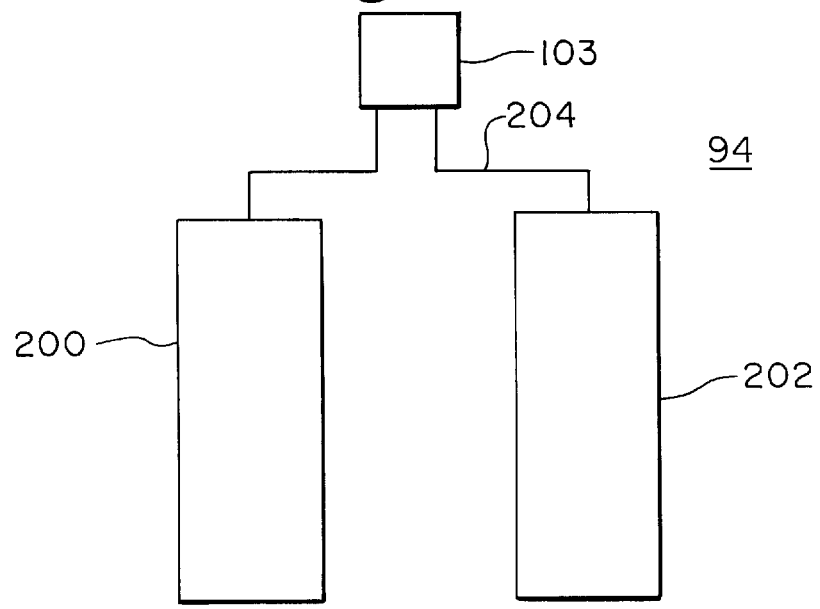

FIG. 9c shows an alternate arrangement for the HVPG electrode assembly 94. In this embodiment, each electrode 200, 202 is attached to the connector 103 via a lead wire 204. In the embodiment shown in FIG. 9c, one electrode wraps around the right side of a leg, just below the knee, and the other electrode wraps around the left side of the leg, just below the knee.

Figure 9D:
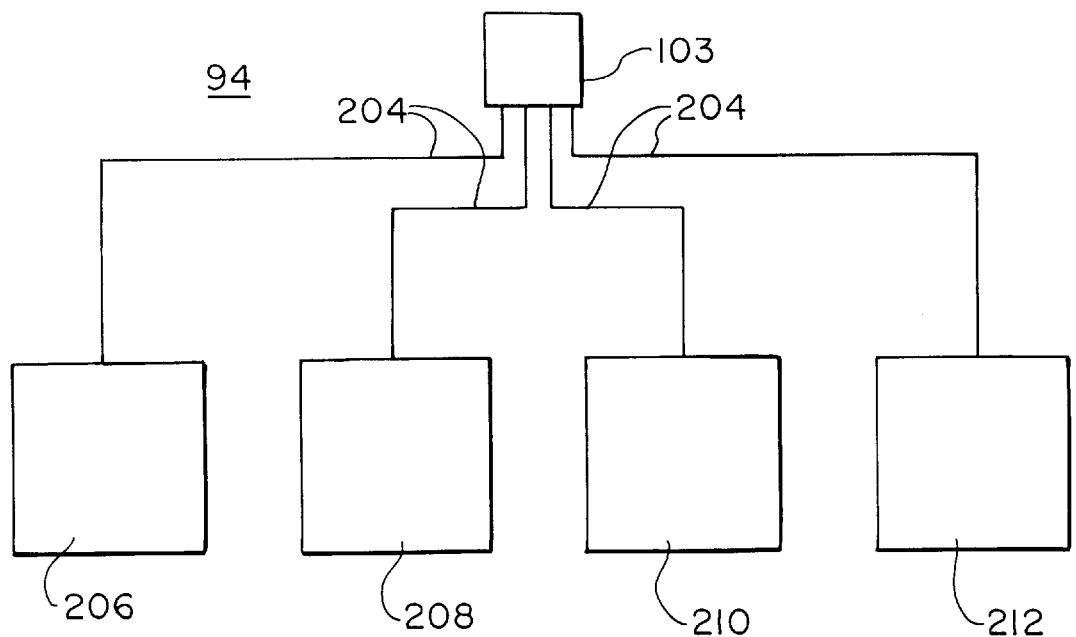
Figure 9E:
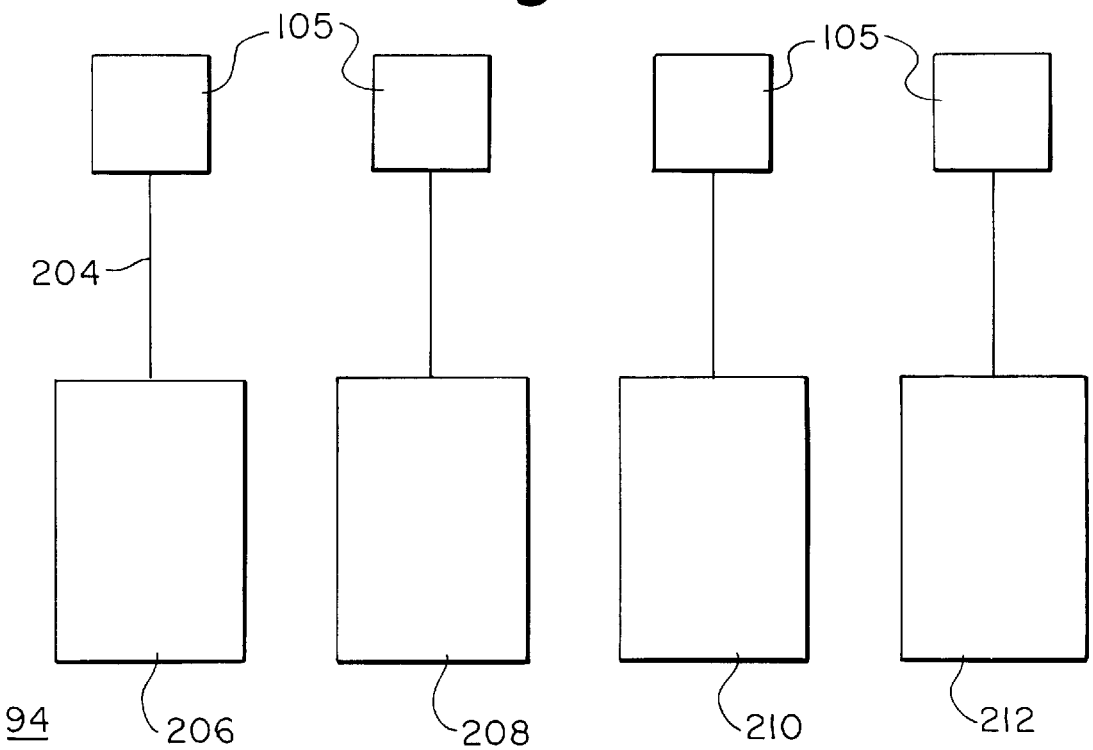

FIG. 9d shows another alternate embodiment of the HVPG electrode assembly 94. In this embodiment, each of the electrodes 206, 208, 210, 212 are connected to connector 103 via a lead wire 94. In this embodiment, two electrodes 206, 208 connect to the front and back of the leg, on the right side, just below the knee, and two electrodes 210, 212 connect to the front and back of the left side of the leg, just below the knee. The embodiment shown in FIG. 9e is the same as FIG. 9d, except that each lead wire 94 would have a separate connector 105. This embodiment may be used to the multi-pin connector 92 shown in FIG. 5a.

Figure 9F:
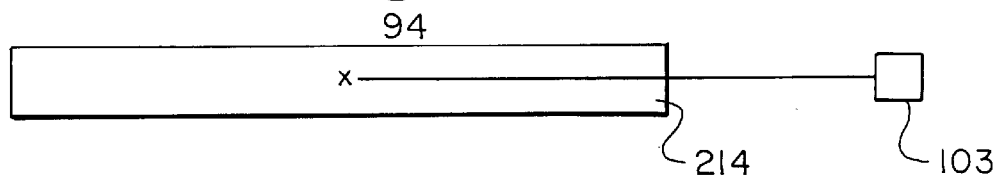

FIG. 9f shows another alternate embodiment of the HVPG electrode assembly 94. In this embodiment, one long electrode 214 is connected to connector 103 via lead wire 94. In this embodiment, the electrode wraps around the leg, just below the knee.

Operation

In use, a user sets the HVPG mode for a selected or recommended treatment time or in the "Auto" position, which provides a preset treatment, and the NMS mode for a given number of repetitions (i.e., muscle contraction/stretch movements or muscle flexures). Generally, the HVPG mode is started and allowed to run for a selected period of time before the user starts the NMS mode. The NMS mode is started by turning on the NMS on/off amplitude switch 32; and setting the desired amplitude. At start, the NM provides stimulation for 20 seconds in order to provide the user with time to adjust the amplitude. The NMS mode runs, along with the HVPG mode, until the set number of repetitions have been completed, and then automatically shuts off. The number of repetitions set and the number completed may be digitally displayed. The HVPG mode continues to run after the NMS mode is completed, until the treatment period selected by the user is completed. The unit automatically shuts down. To reset the unit for the next treatment session, a user is required to shut down both modes using the on/off controls and reset the treatment cycle parameters. All user inputs will be selected by the setting of the user controls, i.e., the software will not interface with the user, but rather, will control the interface between each setting on each control to select the desired output. However, user inputs could be selected by patient interface microprocessor using a menu style program.

The external interfaces, i.e., inputs and outputs, of the software system include the following inputs: a crystal oscillator (or system clock), an NMS repetition switch setting (eight-position binary input), timer switch (eight-position binary input), an NMS off time switch (three-position binary input), power interrupt signal and system reset signal. The outputs comprise: a HVPG output (frequency, pulse pair spacing), complementary NMS output (ramp up/down, pulse width, duration, frequency), HVPG diode pulse frequency and an NMS diode pulse frequency.

The following system features are accomplished by the software and do not require interaction with the user:

HVPG output

The pulse pair spacing is 100 microseconds ("$\mu$sec") at a frequency of 100 Hz and 4 Hz. Treatment time relative to the setting on the switch is 10, 20, 30, 45, 60, 90, 120 minutes and continuous (4 hours). For treatment times 30 minutes or longer, frequency decreases to 4 Hz over a 12-second interval and runs at 4 Hz for the last 14 minutes and 48 seconds of the selected treatment time. Output will shut off after the set time is expired. If the treatment times are set for 10 or 20 minutes, the HVPG output will be at 100 Hz and the output will be shut off after the set time is expired. If the HVPG output is set in the auto mode, the system will sense the completion of the NMS treatment time, at the end of which the HVPG output will run at 100 Hz for 2 minutes and decrease to 4 Hz in 12 seconds, then run for 14 minutes and 48 seconds at 4 Hz and shut off.

NMS output

The pulse width is 300 $\mu$sec each phase, 600 $\mu$sec for biphasic pulse. The NMS pulse frequency is 33.33 Hz. The output ramps up for 3 seconds, remains for 10 seconds at the set level, and ramps down for 1 second. The ramp up and ramp down is controlled by varying the pulse width from 0 to 300 $\mu$sec for each phase of the NMS biphasic pulse. The ramp up and ramp down function is linear. The first repetition of each selected number of repetitions will have a 20-second on time. The NMS "on" LED is on when the NMS mode is on and flashes at 33.33 Hz when output is delivered for each repetition. For the off-time between repetitions, the NMS LED is on for one half second, off for half second, on for half second, etc., over the total off-time. Note that these characteristics may be made programmable or selectable over a given range.

Interface Between Outputs

The HVPG time setting on the timer control will override the NMS treatment time setting (defined by the number of repetitions and the time between each repetition) to shut off the outputs of both modes except when the HVPG is placed in an "auto" (continuous) mode. When the HVPG is set in the auto mode and an NMS cycle is run and completed, the system senses the completion of the NMS cycle, runs for 17 minutes and shuts down. For the first 2 minutes of the 17, the HVPG output will be 100 Hz, then will ramp down to 4 Hz in 12 seconds, run at 4 Hz for 14 minutes and 48 seconds (see FIG. 10).

When the NMS mode is on with the HVPG mode on or off, and the NMS treatment time (based on the number of repetitions selected and the selected time between each repetition) is longer than the time set on the timer control, the timer setting will override the NMS treatment time and shut off the NMS output and the HVPG output when the time set on the timer expires. Generally, the treatment time begins, at the start of the HVPG cycle if both modes are on, or begins at the start of the NMS cycle if only the NMS mode is being run, and the timer always overrides the NMS treatment time defined by the number of repetitions whether the HVPG mode is running or not.

When the NMS mode is on with the HVPG mode on or off, and the HVPG treatment time is set for 30 minutes, all NMS treatment times greater than 13 minutes will shut off at 13 minutes (see FIG. 13). When the NMS mode is on with the HVPG mode on or off, and the HVPG treatment time is set for 45 minutes, all NMS treatment times greater than 28 minutes will shut off at 28 minutes (see FIG. 12). When the HVPG mode is off and not set in the auto mode, and the NMS is turned on and the treatment time is less than the treatment set on the timer, the NMS may be recycled after the first NMS treatment is completed by shutting the NMS control off and turning it back on. The NMS may be recycled until the set time on the timer has expired for 25 minutes or less, or may be recycled until the time set on the timers expired minus 17 minutes for 30 minutes or greater (not including the auto mode).

When the HVPG mode is running and the NMS mode is completed before the HVPG mode is completed, the HVPG mode will complete its set cycle time, go to the 17 minute cool down cycle and complete the cool down cycle when the timer is set on 30 minutes or greater (see FIG. 11). For timer settings of 25 minutes or less, the HVPG mode will complete its cycle at 100 Hz. If the NMS mode is running and the HVPG mode is turned on, the HVPG mode will shut off at the treatment time set on the timer minus the time the NMS mode has been on before the HVPG mode is turned on. If this is less than the time required to complete the NMS mode, both modes will shut off. If the timer is set in the auto mode and the NMS mode is run while the HVPG mode is off, the NMS mode will complete its cycle as defined by the number of repetitions and the time between the repetition, then shut off.

FIGS. 10–13 are provided to exemplify the operational sensing and self-control capabilities of the present invention. FIG. 10 depicts the operation of the device with the timer set in the auto mode, and the HVPG and NMS both on. If the NMS cycle is completed, the HVPG output continues to run at 100 Hz for 2 minutes. This output level will decrease to 4 Hz over 12 seconds, and continue for 14 minutes, 48 seconds, then shut off. FIG. 11 depicts the device set to a selected time with both HVPG and NMS running. If the NMS mode is completed 17 minutes or more before the end of the HVPG mode, the HVPG output continues to run at 100 Hz up to the last 15 minutes of the HVPG set time. For the last 15 minutes of the set time, it decreases to 4 Hz over 12 seconds, continues for 14 minutes, 48 seconds, then shuts off. FIG. 12 depicts the device set to from 30 to 120 minutes with both outputs on. The NMS mode will shut off 17 minutes before the end of the selected time whether on not the NMS cycle has been completed. The HVPG output continues to run at 100 Hz for 2 minutes, decreases to 4 Hz over 12 seconds, continues for 14 minutes, 48 seconds, then shuts off. If the time is set for 10 or 20 minutes, both modes shut off at the end of the time. When only the NMS mode is on, the NMS output will stop 17 minutes before the end of the selected time for settings from 30–120 minutes and, for setting from 10–20 minutes will shut off after the set time expires.

Although the present invention advantageously operates in both the HVPG and NMS modes at the same time, they may be operated separately. The general sequence of operations for using the system in the HVPG mode are as follows:

The user sets the treatment time on the timer;

The system cycle is initiated in the HVPG mode by the user turning the HVPG mode on/off amplitude control on and adjusting the amplitude to the desired level;

The system delivers output for the amount of time set on the timer;

When the time set on the timer is complete, the system shuts down;

When the unit completes the cycle, to prevent current drain on the power source, the user should turn the HVPG control to the off position;

When the unit is shut down, the system is reset and the user can recycle the system at the same time by turning the HVPG control off and on again;

The system may be shut down before the treatment set on the timer is completed by turning the HVPG control to the off position; and The user can change the cycle time any time during treatment by changing the setting on the timer.

The sequence of operation using the system in the NMS mode is as follows:

The user sets the time between the output cycles (repetitions) on the NMS off time switch;

The user sets the number of repetitions desired for the treatment cycle on the "Reps" switch;

The timer switch should generally be set in the "auto" mode;

If the user sets the timer for a period of less than the cycle time established by the number of repetitions and the off time between each repetition, the timer will override the NMS settings and shut down then the time set on the timer is completed;

The system cycle is initiated in the NMS mode by the user turning the NMS control on and adjusting the amplitude;

When the number of repetitions or set time on the timer is complete, the system will shut down.

When the unit completes the treatment cycle, to prevent current drain on the power source, the user should turn the NMS control to the off position;

When the unit is shut down, the system resets (the user can recycle by turning the NMS control off and on again);

The system may be shut down before the treatment is completed by the user turning the NMS control to the off position;

The user can change the cycle time at any time between treatments by changing the number of repetitions and the time between each repetition, or the time set on the timer;

If the cycle time is increased, the system will continue to operate until the increased cycle time is completed; and If the cycle time is decreased, the system will shut off if the system has been running for a longer time than the revised setting. If the system has been running for less time than the revised setting, it will continue to operate until the time on the new setting has expired, then shut off.

The sequence of operations in the HVPG and NMS modes together may be outlined as follows:

The user sets the desired treatment time on the timer for the HVPG treatment;

In the auto mode, the HVPG detects the end of the NMS cycle, the system goes into the cool down HVPG output cycle triggered by the completion of the NMS cycle;

Following the cool down, the unit shuts down. Therefore, when both modes are used together, it is recommended that the timer be set in the auto position;

The user sets the time between the output cycles (repetitions on the NMS off time switch);

The user sets the number of repetitions desired for the treatment cycle on the "Reps" switch;

The system cycle is initiated in the HVPG mode by the user turning the HVPG control on and adjusting the amplitude;

After a prescribed treatment time has elapsed in the HVPG mode, the system cycle is initiated in the NMS mode by the user turning on the NMS control and adjusting the amplitude;

If the HVPG cycle was set in the auto mode or for a period longer than the HVPG mode on time before the NMS mode was started, plus the NMS mode treatment time, plus the 17 minute cool down time, the unit will sense the end of the NMS mode, go into the 17 minute cool down cycle, and upon completion, shut the output down;

When the unit is shut down, the system is reset, the user can recycle the system at the same settings by turning the controls off and on again;

The system may be shut down before the treatment is completed by the user by turning the controls off; and If only one control is shut off by the user, the mode left on will continue to operate in accordance with the way the software controls the cycle.

It is anticipated that the electrotherapy device will include a housing or case 20 capable of adapting to a mobile or stationary environment, and to clinic, hospital or home use. The case 20 may be labeled or provided with instructional information as necessary. As shown in FIG. 2, the cable 102 ideally includes a 12 to 18 inch coiled portion, extendable to 5 to 6 feet, and is split adjacent to the distal end into different lengths to facilitate the placement of the electrodes. The connection to the electrodes is preferably a .060 diameter recessed pin type connector that is commercially available. The size of the common electrode is about four by seven inches, but any size may be used as long as it is sufficiently large to involve both medial and lateral muscle bellies for achieving proper contraction.

The system as marketed will be made up of: a generator (i.e., the housing 20 and circuitry therein), a cable assembly, a large dispersive electrode (4 in.×7 in.), a medium size active electrode for the NMS mode (2 in.×4 in.), from one to four active electrodes for the HVPG mode, four "AA" alkaline batteries and a carrying case (existing Rehabilicare hard case, typically made from high impact thermoplastic or the like, with standard labelling). Options may include: four "AA" size rechargeable batteries with a charger, additional and/or different size and style of electrodes and line powered Repak™ (i.e., D.C. power supply).

HVPG and NMS outputs having a single, fixed parameter value as described above are selected for the preferred embodiment of the invention, but it should be appreciated that the outputs may have any selected or adjustable value within the customary ranges for accomplishing muscle stimulation and pain relief. Additionally, the electrotherapy device of the present invention may be made available with more than one NMS channel and HVPG channel, and such additional electronic components and controls as are necessary for the additional NMS channel and HVPG channel.

Although a description of a preferred embodiment has been presented, various changes, including those mentioned above, could be made without deviating from the spirit of the present invention. It is desired, therefore, that reference be made to the appended claims rather than to the foregoing description to indicate the scope of the invention.

What is claimed is:

1. An electrotherapy device, comprising:
    (a) a first electrical stimulation device for providing a first type of electrical stimulation,
    (b) a second electrical stimulation device for providing a second type of electrical stimulation that is different from the first type of electrical stimulation; and
    (c) a controller means for respectively providing timing, repetition counting, and trigger signals to said first and said second electrical stimulation devices simultaneous to provide different types of electrical stimulation to a patient from both the first and second electrical stimulation devices simultaneously.

2. The device of claim 1, wherein the first electrical stimulation device comprises a pulsed galvanic output circuit for providing high voltage pulsed galvanic stimulation.

3. The device of claim 2, wherein the second electrical stimulation device comprises a neuromuscular voltage output circuit for providing neuromuscular stimulation.

4. The device of claim 3, further comprising a cable assembly for accommodating the pulsed galvanic and neuromuscular outputs.

5. The device of claim 4, further comprising an electrode assembly adapted to be connected to the cable assembly for accommodating the pulsed galvanic and neuromuscular outputs.

6. The device of claim 1, wherein the first and second stimulations comprise different waveforms.

7. The device of claim 1, wherein the first and the second types of electrical stimulations comprise first and second types of stimulation modes deliverable to a patient.

8. The device of claim 1, wherein the first and the second types of electrical stimulations have different frequencies.

9. The device of claim 8, wherein the first and the second type stimulations are delivered simultaneously to a patient with an external method.

10. An electrotherapy device, comprising:
    a high voltage pulsed current electrotherapy stimulation device for providing generally short duration, low amp, high voltage, constant charge electrical galvanic pulses to a patient to reduce pain;
    a neuromuscular stimulation electrotherapy device for providing neuromuscular stimulative electrical pulses to a patient to re-educate and prevent atrophy of muscle tissue; and
    a controller means for operating and controlling the high voltage pulsed current electrotherapy device and the neuromuscular stimulation electrotherapy device simultaneously to produce the high voltage stimulation and neuromuscular stimulation so that at least a portion of each of said stimulations are provided to the patient simultaneously.

11. The device according to claim 10, wherein the pulsed galvanic output is a high voltage pulsed galvanic exponential spike, the neuromuscular output is a symmetric biphasic square wave, and the timing and frequency of the high voltage pulsed galvanic exponential spike and the symmetric biphasic square wave is configured such that they do not overlap.

12. The device according to claim 10, wherein the controller is controlled by a crystal oscillator for providing a system clock, a neuromuscular stimulation repetition switch setting of a multi-position binary input, a timer switch of a multi-position binary input, a neuromuscular stimulation off time switch of multi-position binary input, a power interrupt signal and a system reset signal.

13. The device according to claim 12, wherein the controller output comprises a high voltage pulsed galvanic stimulation output, a complementary neuromuscular stimulation output, a high voltage pulsed galvanic stimulation indicator LED pulse frequency and a neuromuscular stimulation indicator LED pulse frequency.

14. The device according to claim 10, wherein the neuromuscular stimulation pulse's voltage output is a symmetric biphasic pulse output with an amplitude of 0 to about 100 mA peak and pulse rate of about 33 Hz.

15. The device according to claim 14, wherein the symmetric biphasic pulse has a pulse width ramping from 0 to about 300 microsecond.

16. The device according to claim 14, wherein the ramp up time of neuromuscular stimulation modality output is about 3 seconds.

17. The device according to claim 16, wherein the on time of neuromuscular stimulation modality output is about 10 seconds.

18. The device according to claim 17, wherein the ramp down time of neuromuscular stimulation modality output is about 1 second.

19. The device according to claim 14, wherein the off time between stimulation cycles is adjustable among 10, 20, or 30 seconds.

20. The device according to claim 19, wherein the number of stimulation cycles is adjustable in increments of 5 repetitions from 5 repetitions to 50 repetitions.

21. The device according to claim 10, wherein the neuromuscular stimulation pulse's voltage output is a symmetric biphasic square wave output with an amplitude of 0 to about 100 mA peak, and a pulse rate of about 33 Hz.

22. The device according to claim 21, wherein the symmetric biphasic square wave has a pulse width of ramping from 0 to about 300 microsecond.

23. The device according to claim 21, wherein the ramp up time of neuromuscular stimulation modality output is about 3 seconds.

24. The device according to claim 23, wherein the on time of neuromuscular stimulation modality output is about 10 seconds.

25. The device according to claim 24, wherein the ramp down time of neuromuscular stimulation modality output is about 1 second.

26. The device according to claim 10, wherein the pulsed galvanic output is a high voltage pulsed galvanic modality having the characteristics comprising a wave form as a pulsed galvanic, monophasic exponential spike, delivered in pulse pairs about 100 microseconds apart.

27. The device according to claim 26, wherein the pulsed galvanic output voltage is adjustable between about 0 to about 350 volts.

28. The device according to claim 27, wherein the pulsed galvanic output pulse width is 7 microseconds at 50% peak.

29. The device according to claim 28, wherein the pulsed galvanic output pulse pair high frequency is about 100 Hz, and the low frequency is about 4 Hz.

30. The method according to claim 28, wherein the high voltage pulsed galvanic mode continues to run after the neuromuscular stimulation mode is completed.

31. The method according to claim 29, wherein the high voltage pulsed galvanic mode continues to run until the treatment period selected by the user is completed.

32. An electrotherapy device, comprising:
a neuromuscular voltage output circuit for providing a neuromuscular voltage;
a pulsed galvanic output circuit for providing pulsed galvanic output;
a cable assembly for accommodating the neuromuscular and galvanic outputs simultaneously; and
an electrode assembly for accommodating the neuromuscular and galvanic outputs simultaneously.

33. The electrotherapy device according to claim 32, wherein the neuromuscular circuit generates a biphasic square wave output.

34. The electrotherapy device according to claim 32, wherein the pulsed galvanic output comprises monophasic high voltage galvanic pulsed pair output.

35. The electrotherapy device according to claim 32, further comprising a micro controller operably coupled to the neuromuscular and pulsed galvanic output circuits.

36. The electrotherapy device according to claim 32, wherein the electrode assembly comprises a common passive electrode, an active high voltage electrode and an active neuromuscular electrode.

37. The electrotherapy device according to claim 36, wherein the cable assembly comprises a cable member with a proximal end and a distal end, said cable member bifurcated adjacent to the distal end for being coupled to said electrodes.

38. The electrotherapy device according to claim 37, wherein the proximal end of the cable member carries a first part of a two part connector for releasably connecting the cable member to the device, the second part complementary to the first and carried by the device.

39. The device according to claim 37, wherein the cable between the proximal end and the distal end is a coiled multi-conductor cable.

40. The device according to claim 37, wherein the bifurcated distal end includes one distal connector used with an active neuromuscular stimulation electrode, one distal connector used with a common dispersive electrode and one distal connector used with at least one high voltage pulsed galvanic stimulation electrode.

41. The device according to claim 40, wherein the distal connector used with the high voltage pulsed galvanic stimulation electrodes is a multi-pin connector for connecting a plurality of high voltage pulsed galvanic stimulation electrodes when the high voltage pulsed galvanic stimulation electrodes are not connected to a common electrode connector.

42. A method of electrotherapy comprising the steps of:
providing generally high voltage pulses to a patient to reduce pain
substantially simultaneously with at least a portion of the high voltage pulses providing neuromuscular stimulation biphasic square wave pulses to the patient to re-educate and prevent atrophy of muscle tissue;
said high voltage and said neuromuscular stimulation pulse are provided to generally the same region of the patient; and
further comprising providing a controller adapted to operate and control both the generally high voltage pulses and the neuromuscular stimulation pulses, whereby the high voltage and stimulation pulses are provided to the patient simultaneously.

43. The method according to claim 42, including using different pulse modes for the high voltage and neuromuscular stimulation pulses.

44. The method according to claim 42, including using a waveform for the high voltage pulse that is different from the neuromuscular stimulation pulse.

45. The method according to claim 42, wherein the mode for providing high voltage pulses to a patient is started and allowed to run for a selected period of time before the user starts the neuromuscular stimulation mode for providing neuromuscular stimulation pulses.

46. The method of claim 42, further comprising the steps of decreasing the frequency of the high voltage pulsed galvanic stimulation output to 4 Hz over a 12-second interval and running at about 4 Hz for about the last 14 minutes of a selected treatment time when treatment times are 30 minutes or longer, and shutting off the output after the set time is expired.

47. The method of claim 42, wherein the frequency of the high voltage pulsed galvanic stimulation output is about 100 Hz and the output shuts off after a set time is expired when treatment times are set for about either 10 or 20 minutes.

48. The method of claim 42, wherein when the high voltage pulsed galvanic stimulation output is set in an automatic mode, a control system will sense the completion of a neuromuscular stimulation treatment time, at the end of which the high voltage pulsed galvanic stimulation output will run at about 100 Hz for about 2 minutes and will decrease to about 4 Hz in about 12 seconds, then run for about 15 minutes at 4 Hz and then shut off.

49. The method of claim 42 further comprising steps for controlling the device comprising the steps of:
   activating a power on/reset to initialize inputs and outputs, to clear any RAM and to enable a real time interrupt at 10 ms;
   providing a 10 ms pace loop which generates 10, 30, and 50 ms timing triggers; and
   activating output triggers to enable high voltage pulsed galvanic stimulation signals at 100 micro second spacing and 100 pulse pairs/second.

50. The method according to claim 49, wherein when the high voltage pulsed galvanic stimulation output is set in an auto mode and a neuromuscular stimulation cycle is run and completed, the system will sense the completion of the neuromuscular stimulation cycle, run for 17 minutes and shut down, wherein for the first 2 minutes of the 17 minutes the high voltage pulsed galvanic stimulation output will be 100 hz, then will ramp down to 4 Hz in 12 seconds, run for 14 minutes and 48 seconds at 4 hz.

51. The method according to claim 49, further comprising the steps of:
   turning on a high voltage pulsed galvanic stimulation LED for 1 ms;
   driving the output for each phase of neuromuscular stimulation according to pulse width number;
   turning a neuromuscular stimulation LED on and off and providing a one second blink rate of the neuromuscular stimulation LED during neuromuscular stimulation off-time;
   generating a pulse width number for ramping according to input switches and timing of a neuromuscular stimulation cycle;
   counting neuromuscular stimulation cycles and comparing with "Reps" switch setting for neuromuscular stimulation shut-off;
   changing the frequency of the high voltage pulsed galvanic stimulation to about 4 Hz during the last 15 minutes when required as determined by a timer setting;
   comparing total stimulation time with the switch setting and initiating a shut off at a correct time; and
   updating switch setting registers at about each half second;
   maintaining this sequencing as long as the power is on and until the controller shuts down.

52. The method according to claim 51 wherein when the timer is set in the auto mode and the high voltage pulsed galvanic stimulation and the neuromuscular stimulation are running simultaneously and if the neuromuscular simulation cycle is complete, a sensor is triggered to continue operating the high voltage galvanic stimulation at 100 HZ for two minutes.

53. The method according to claim 51, wherein when the neuromuscular stimulation mode is on with the high voltage pulsed galvanic stimulation mode on or off, and a neuromuscular stimulation treatment time based on the number of repetitions selected and the selected time between each repetition is longer than the time set on a timer control, the timer setting will override the neuromuscular stimulation treatment time and shut off the neuromuscular stimulation output and the high voltage pulsed galvanic stimulation output when the time set on the timer expires.

54. The method according to claim 53, wherein the treatment time begins at the start of the high voltage pulsed galvanic stimulation cycle.

55. The method according to claim 54, wherein the treatment time begins at the start of the neuromuscular stimulation cycle if only the neuromuscular stimulation mode is being run.

56. The method according to claim 55, wherein the timer always overrides the neuromuscular stimulation treatment time defined by the number of repetitions independent of the running condition of the high voltage pulsed galvanic stimulation modes.

57. The method according to claim 52 wherein the high voltage galvanic stimulation cycle at 100 HZ is reduced to 4 HZ over a 12 second period and continued for 14 minutes and 48 seconds before shut off.

58. The method according to claim 57, wherein when the high voltage pulsed galvanic stimulation mode is off and not set in the auto mode, and the neuromuscular stimulation is turned on and the treatment time is less than the treatment set on the timer, the neuromuscular stimulation is recycled after the first neuromuscular stimulation treatment is completed by shutting the neuromuscular stimulation control off and turning it back on.

59. The method according to claim 58, wherein when the high voltage pulsed galvanic stimulation mode is off and not set in the auto mode, and the neuromuscular stimulation is turned on and the treatment time is less than the treatment set on the timer, the neuromuscular stimulation is recycled until the set time on timer has expired for 25 minutes or less.

60. The method according to claim 59, wherein when the high voltage pulsed galvanic stimulation mode is off and not set in the auto mode, and the neuromuscular stimulation is turned on and the treatment time is less than the treatment set on the timer, the neuromuscular stimulation is recycled until the set time on a timer has expired 17 minutes for use when settings at 30 minutes or greater.

61. The method according to claim 57, wherein when the high voltage pulsed galvanic stimulation mode is running and the neuromuscular stimulation is completed before the high voltage pulsed galvanic stimulation mode is completed, the high voltage pulsed galvanic stimulation mode will complete its set cycle time, go to the 17 minutes cool down cycle and complete the cool down cycle when the timer is set on 30 minutes or greater; the high voltage pulsed galvanic stimulation mode will complete its cycle at 100 Hz for timer settings of 25 minutes or less.

62. The method according to claim 61, wherein when the neuromuscular stimulation mode is running and the high voltage pulsed galvanic stimulation mode is turned on, the high voltage pulsed galvanic stimulation mode will shut off at the treatment time set on the timer minus the time the neuromuscular stimulation mode has been on before the high voltage pulsed galvanic stimulation mode is turned on, and if this is less than the time required to complete the neuromuscular stimulation mode, both modes will shut off.

63. The method according to claim 62, wherein when the timer is set in the auto mode and the neuromuscular stimulation mode is run while the high voltage pulsed galvanic stimulation mode is off, the neuromuscular stimulation mode will complete its cycle as defined by the number of repetitions and the time between the repetition, then shut off.

* * * * *